United States Patent [19]

Stogryn et al.

[11] Patent Number: 4,487,967

[45] Date of Patent: Dec. 11, 1984

[54] PROCESS FOR PREPARING SECONDARY AMINOETHER ALCOHOLS

[75] Inventors: Eugene L. Stogryn, Edison; W. S. Winston Ho, Annandale; Angelo A. Montagna, Summit; Guido Sartori, Linden, all of N.J.

[73] Assignee: Exxon Research & Engineering Co., Florham Park, N.J.

[21] Appl. No.: 565,097

[22] Filed: Dec. 23, 1983

[51] Int. Cl.$^3$ .................... C07C 85/00; C07C 85/02
[52] U.S. Cl. .................... 564/474; 564/447
[58] Field of Search ................ 564/447, 474

[56] References Cited

U.S. PATENT DOCUMENTS

| | | | |
|---|---|---|---|
| 2,355,337 | 8/1944 | Spence | 564/474 |
| 2,928,877 | 3/1960 | Saul et al. | 564/447 X |
| 3,070,552 | 12/1962 | Tesoro et al. | 564/474 X |
| 3,660,319 | 5/1972 | Yeakey | 564/474 X |
| 3,708,539 | 1/1973 | Fenton | 564/447 X |

*Primary Examiner*—Paul F. Shaver
*Attorney, Agent, or Firm*—Henry E. Naylor

[57] ABSTRACT

The present invention relates to a process for selectively preparing severely sterically hindered secondary aminoether alcohols by reacting a primary amino compound with a polyalkenyl ether glycol in the presence of a hydrogenation catalyst at elevated temperatures and pressures. The severely sterically hindered secondary aminoether alcohols are useful in acid gas scrubbing processes, particularly in the selective removal of $H_2S$ from gaseous streams containing $CO_2$ and $H_2S$.

10 Claims, 2 Drawing Figures

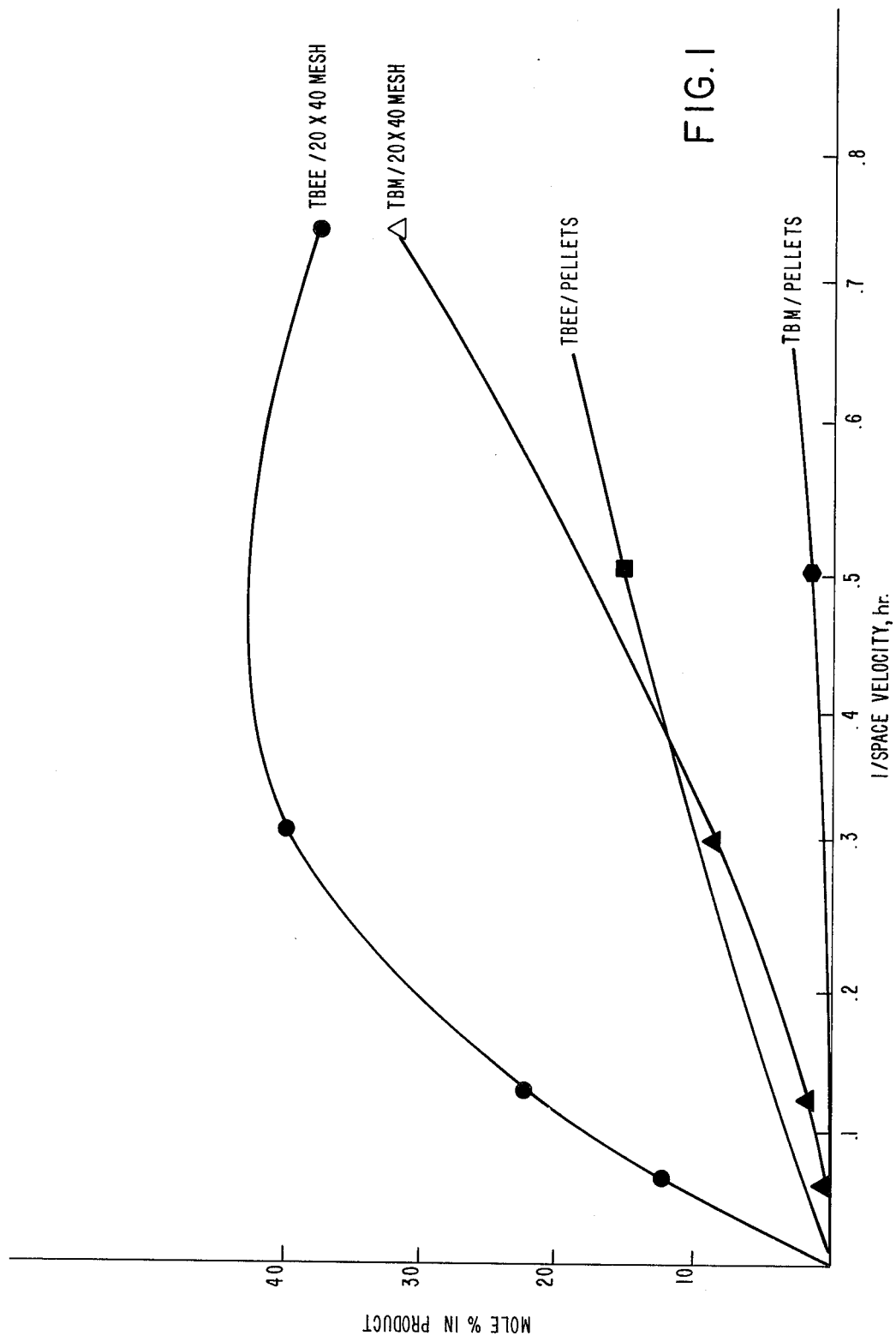

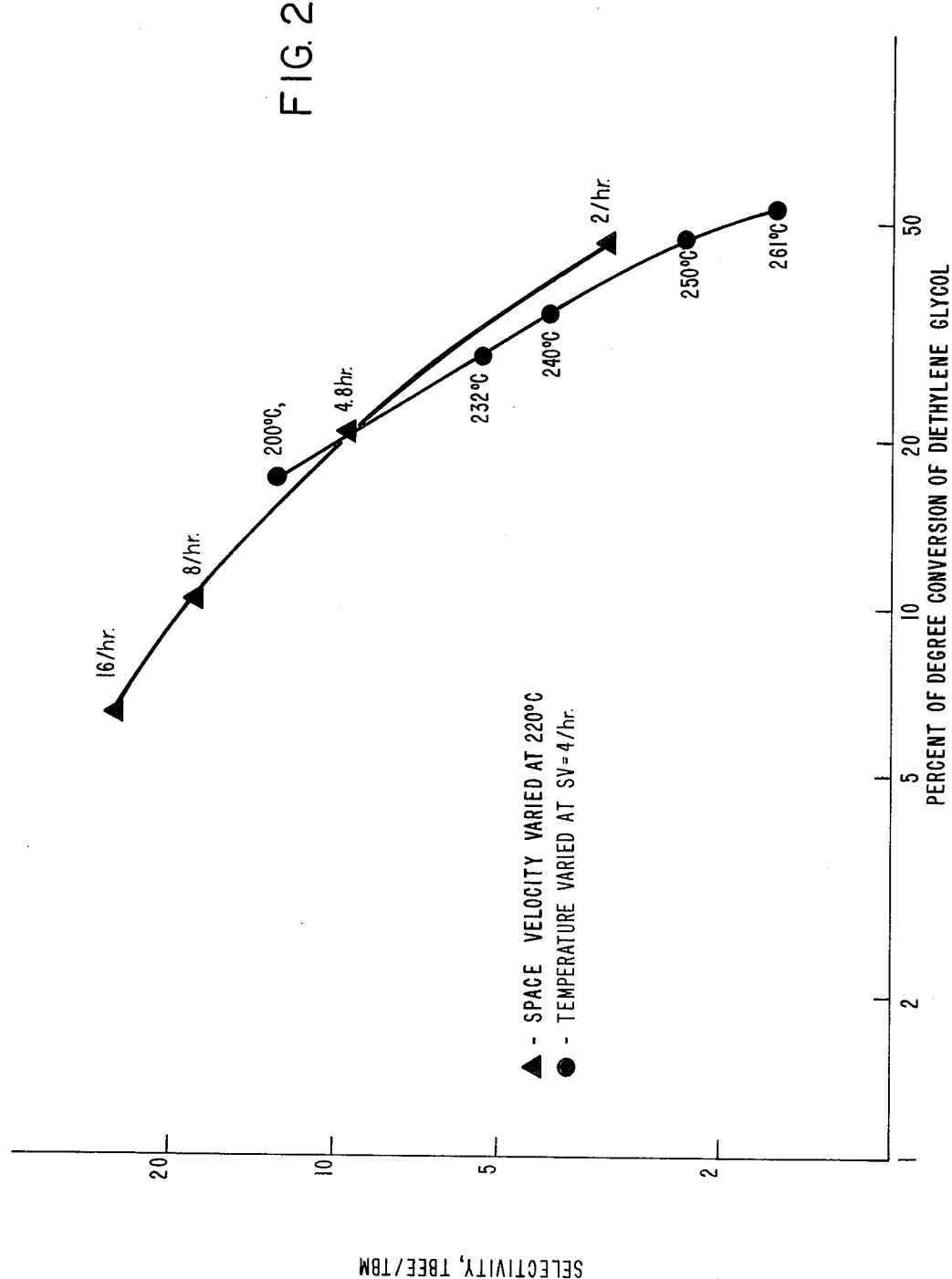

PROCESS FOR PREPARING SECONDARY AMINOETHER ALCOHOLS

BACKGROUND OF THE INVENTION

1. Field of the Invention

The present invention relates to a process for selectively preparing severely sterically hindered secondary aminoether alcohols by reacting a primary amino compound with a polyalkenyl ether glycol in the presence of a hydrogenation catalyst at elevated temperatures and pressures. The severely sterically hindered secondary aminoether alcohols are useful in acid gas scrubbing processes, particularly in the selective removal of $H_2S$ from gaseous streams containing $CO_2$ and $H_2S$.

2. Description of Related Patents and Publications

Recently, it was shown that severely sterically hindered secondary aminoether alcohols are superior to methyldiethanolamine (MDEA) in scrubbing $H_2S$ from gaseous streams containing the same, especially in selectively removing $H_2S$ from normally gaseous mixture containing $CO_2$ and $H_2S$. Such processes are disclosed and claimed in U.S. Ser. No. 339,891, filed Jan. 18, 1982, now U.S. Pat. No. 4,405,585, the disclosure of which is incorporated herein by reference. These compounds may be produced by processes such as reacting a primary amine having a bulky carbon atom grouping with a haloalkyoxyalkanol. This process is more fully disclosed in allowed U.S. Ser. No. 339,892, filed Jan. 18, 1982, and allowed U.S. Ser. No. 453,452 filed Dec. 27, 1982, the disclosures of which are incorporated herein by reference. One disadvantage inherent in the use of haloalkoxy-alkanols is the need to employ corrosion-resistant equipment due to formation of halide by-products and the necessity to remove these halide by-products. Also, such processes require numerous purification steps including the use of caustic for the conversion of by-product amine hydrochloride salts into inorganic chloride and a subsequent filtration. Such purification procedures contribute to increasing the costs in producing the desired amine product. In addition, disposal of large quantities of inorganic chlorides produced in this process may present environmental problems.

The amination of alcohols with ammonia, primary and secondary amines by hydrogenation-dehydrogenation catalysis is well known as evidenced by ENCYCLOPEDIA OF CHEMICAL TECHNOLOGY, Vol. 2, 3rd Edition, p.276. However, very bulky amines appear ineffective in this process.

U.S. Pat. No. 3,223,734 states that amines with branching at the carbon adjacent (alpha) to the amino moiety are much less preferred for the amine/alcohol amination process due to the inferior results with such reactants. U.S. Pat. No. 3,366,687 describes the viability of the amination process using the alpha-branched isopropylamine. There is no disclosure of using the more bulky tertiary alkyl groups in the amination reaction.

Both U.S. Pat. Nos. 3,223,734 and 3,366,687 disclose that barium promoted copper chromite catalysts are capable of giving yields of greater than 60% from the amine/alcohol amination process. Baiker and Richarz, *Tetrahedron Lett*, 1937 (1977), reported that the dimethylamine/alcohol reaction operated in a continuous mode (fixed-bed reaction) to give over 96% conversion to tertiary amine when a copper-chromium oxide catalyst (BASF H3-107) was used. Murahask, *Chem. Comm.*, 931 (1974), has described the use of palladium black to catalyze, in 98% yield, the amination of benzyl alcohol with $C_6$ amines.

In contrast to these disclosures, applicants have found that barium promoted or unpromoted copper chromite and palladium black catalysts do not catalyze the reaction of bulky amines such as tertiary butylamine with diethylene glycol.

The present invention is based on the discovery that when a primary amino compound having steric hindrance is reacted with a polyalkenyl ether glycol or a primary amino compound is reacted with a polyalkenyl ether glycol having steric hindrance in the presence of a hydrogenation-dehydrogenation catalyst, a severely sterically hindered secondary aminoether alcohol is produced. Unexpectedly, the resulting severely sterically hindered secondary aminoether alcohol will not react further with additional glycol reactant to form a tertiary amine even when excess glycol reactant is used. This is in contrast with other processes involving the amination of polyalkenyl ether glycols with primary amino compounds, which typically provide tertiary amines.

SUMMARY OF THE INVENTION

The present invention is directed to a process, batch or continuous, for selectively producing a severely sterically hindered secondary amino compound, comprising reacting:

(a) a primary amino compound having the general formula:

where $R_1$ is selected from the group consisting of secondary or tertiary alkyl radicals having 3 to 8 carbon atoms or cycloalkyl radicals having 3 to 8 carbon atoms, with (b) a polyalkenyl ether glycol having the general formula:

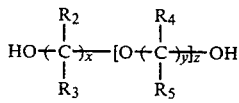

where $R_2$, $R_3$, $R_4$ and $R_5$ are each independently selected from the group consisting of hydrogen, $C_1$ to $C_4$ alkyl radicalsw, and C3–C8 cycloalkyl radicals, with the proviso that if the carbon atom of $R_1$ directly attached to the nitrogen atom is secondary, at least one of $R_2$ and $R_3$ directly bonded to the carbon which is bonded to the hydroxyl group is an alkyl or cycloalkyl radical, x and y are each positive integers independently ranging from 2 to 4, and z is from 1 to 10, preferably 1 to 6, more preferably 1 to 4, said process being carried out in the presence of a catalytically effective amount of a supported Group VIII metal containing hydrogenation catalyst at elevated temperatures and pressures and wherein the mole ratio of amino compound to polyalkenyl ether glycol is less than 2:1 when z is greater than 1.

Preferably $R_1$ is an alkyl radical having 4 to 6 carbon atoms, $R_2$ and $R_3$ are hydrogen and x and y are 2. Most preferably, $R_1$ is tertiary-butyl, $R_2$ and $R_3$ are hydrogen, x and y are 2, and z is 1. When the reactants are so defined the compound tertiarybutylaminoethoxyethanol (TBEE) is produced.

DESCRIPTION OF THE DRAWINGS

FIG. 1 graphically illustrates the mole % of the product, tertiary butylaminoethoxyethanol (TBEE) and by-product, N-tertiarybutylmorpholine against the reciprocal of the space velocity, in hours using the supported trimetallic catalyst 2330 at 200° C.

FIG. 2 graphically illustrates the selectivity of tertiarybutylaminoethoxyethanol over N-tertiarybutylmorpholine against the percent of degree conversion of diethylene glycol using the supported trimetallic catalyst 2330 at various designated temperatures (in °C.).

DETAILED DESCRIPTION OF THE INVENTION

The preferred process of the invention involves the amination of diethylene glycol with tertiarybutylamine in the presence of a catalytically effective amount of a hydrogenation catalyst. The reaction may be illustrated by the following general equations.

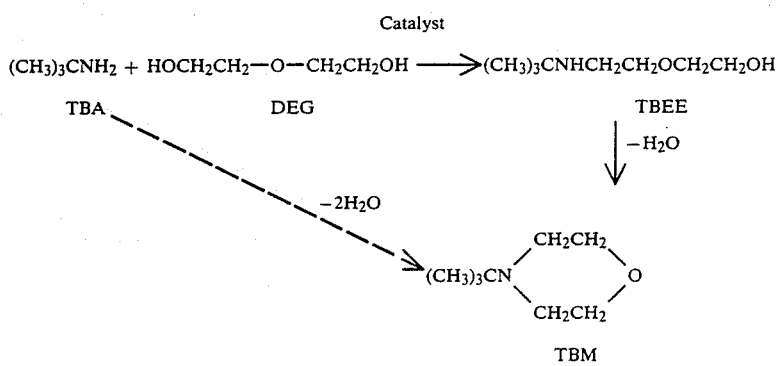

As shown from the above equations, dehydration of either the reactants tertiarybutylamine (TBA) and diethyleneglycol (DEG) or of the desired reaction product tertiarybutylaminoethoxyethanol (TBEE) produces the undesirable by-product N-tertiarybutyl-morpholine (TBM). Thus, by control of the reaction conditions or removing the reaction product as rapidly as possible, for example, in a continuous reaction process, from the reaction zone or by controlling the reaction time one minimizes the amount of TBM formation.

The amination process is carried out under pressure at a temperature ranging from about 160° to about 425° C., preferably from about 180° to about 400° C., and most preferably from about 190° to about 350° C. The pressures in the reactor may range from about 50 to about 3000 psig, preferably from about 100 to about 1000 psig, and most preferably from about 150 to about 750 psig.

The reactor used may include any suitable vessel capable of withstanding the pressures necessary to carry out the amination process. Preferably, the amination process is carried out in a fixed bed reactor whereby the reactants are passed over a fixed bed of the catalyst, either concurrently or countercurrently. Other reactors suitable for use herein include moving bed reactors and continuous stirred reactors. For example, in a continuous stirred reactor the catalyst is circulated and the reactants and reaction products are passed through the reaction vessel at a controlled rate.

The hydrogenation catalyst used in the amination process include, primarily, any of the known supported hydrogenation catalysts. Illustrative hydrogenation catalysts include platinum, palladium and other noble metals such as ruthenium, rhodium, osmium and iridium deposited on inert supports such as carbon, silica, alumina or other refractory oxides, nickel-on-kieselguhr, nickel on inert support, massive nickel or nickel-cobalt or nickel-cobalt-copper coprecipitated with silicate and/or aluminum salts having alumina or kieselguhr supports. Preferred catalysts include coprecipitated nickel and nickel-cobalt-copper supported on silica, alumina, or mixtures thereof. Also preferred is platinum supported on alumina. Still more preferred are catalysts having increasing concentrations of nickel, about 40% to 70% nickel, by weight. Since preferred catalysts include those massive-metal coprecipitated hydrogenation catalysts described in U.S. Pat. Nos. 3,697,445; 4,251,394; 4,251,672; 4,263,173; 4,263,225; 4,273,680; 4,273,939; 4,307,248; 4,318,829; and the metal coprecipitated catalysts containing aluminum and silica disclosed and claimed in U.S. Ser. Nos. 388,966 and 388,967, the disclosures of which are incorporated herein by reference. It is preferred that the catalyst be reduced or activated by a reductant, such as hydrogen prior to use in the amination reaction. This reduction or activation is typically carried out by passing hydrogen over the catalyst at temperatures ranging from 175° to about 400° C., preferably such as 200° to about 350° C. In addition to the catalysts described above, unsupported catalysts such as Raney nickel can be used in the continuous amination process when a continuous stirred reactor is employed.

The concentration of the hydrogenation catalyst is that which is catalytically effective and that amount will generally range from about 0.1 to about 10 weight percent, preferably from about 2 to about 8 weight percent, based on the weight of the reactant charge. The normal pretreatment conditions and handling of the hydrogenation catalyst should be practiced as known to those skilled in the hydrogenation catalyst art.

The theoretical equivalent mole ratio of amino compound to polyalkenyl ether glycol in the reaction charge is 1:1. When the polyalkenyl ether glycol is diethylene glycol the mole ratio of amino compound to diethylene glycol can range from 0.5:1 to 6:1, preferably 2:1 to 4:1. When the polyalkenyl glycol is triethylene glycol or higher, the mole ratio of amino compound to glycol must be kept below 2:1 otherwise the secondary aminoether alcohol would not be favored.

Although the amination of the polyalkenyl ether glycol can be carried out in the absence of a solvent it is often desirable to include an inert solvent in the reaction medium. Preferably the solvent is a cyclic or linear ether or a hydrocarbon containing compound in which the reactants will dissolve. The solvent should be of relatively low molecular weight to facilitate removal from the product of the reaction. The amount of the solvent may vary, but will generally range from about 10 to 50 wt.%, preferably from about 15 to 30 wt.%, based on the weight of the reactants used. Preferred solvents include tetrahydrofuran, dimethylether of ethylene glycol, and toluene.

Reduction of the catalyst may be carried out in situ while conducting the process by the presence of hydrogen. Hydrogen, however, is not essential to conducting the process but is preferably employed, for example, to minimize catalyst deactivation.

It has been observed that the time required for the amination reaction is important in the context of by-product formation. The actual time required in a particular reaction will vary and is dependent upon the specific reactants, catalyst, temperature and pressure used, as well as the size of the batch, as is known to those skilled in the art. Generally, longer reaction times, that is, length of time reactants are in contact with catalyst at reaction temperatures and pressures, lead to formation of by-products including N-tertiary-butylmorpholine and fragmented amines. Similar effects are found at increasing temperatures.

Once the reaction has been completed, the reaction product can be conveniently recovered by known techniques such as solvent evaporation, distillation and the like.

The invention is illustrated further by the following examples which, however, are not to be taken as limiting in any respect. All parts and percentages, unless expressly stated otherwise, are by weight.

EXAMPLE 1

To a 300 ml stainless steel, stirred autoclave there was added 60 g of tertiarybutylamine, 43.5 g of diethylene glycol, 75 ml of toluene and 0.9 g of Ni—$Al_2O_3$—$SiO_2$ catalyst (Harshaw Ni-5132 P). The autoclave was heated to 200° C. under autogenous pressure for 6 hours. The contents were cooled, removed and filtered. The autoclave and filtercake were washed with additional toluene. Distillation at 20 mm Hg pressure gave 35.7 g (54% isolated yield) of tertiarybutylaminoethoxyethanol, having a b.p. of 123°-127° C./20 mm Hg.

EXAMPLE 2 (Comparative)

Following the same procedure as in Example 1, 20 g of tertiary butylamine, 29 g of diethylene glycol, and 0.6 g of Ni-Al catalyst (Degussa B-113W) in 50 ml of toluene were reacted at 200° C. for 6 hours. A yield of 34% tertiarybutylaminoethoxyethanol was isolated from the autoclave reactor.

EXAMPLE 3 (Comparative)

Following the same procedure as in Example 1, 40 g of tertiary butylamine, 29 g of diethylene glycol, and 0.6 of barium promoted copper chromite catalyst (Alfa) in 50 ml of toluene were reacted in the autoclave of 200° C. for 4 hours. Gas chromatography analysis of the substance in the autoclave indicated that no reaction took place.

EXAMPLE 4 (Comparative)

Following the same procedure as in Example 1, 20 g of tertiarybutylamine and 29 g of diethylene glycol in 50 ml toluene were heated in the autoclave with 0.6 g of palladium black catalyst at 200° C. for 20 hours. Gas chromatography analysis of the substance in the autoclave indicated the presence of 1% yield of tertiarybutylaminoethoxyethanol.

EXAMPLE 5

Following the procedure as in Example 1, a number of hydrogenation catalysts were tested for the catalytic amination of diethylene glycol (DEG) with tertiarybutylamine (TBA). The results of the tests are shown in Tables I, II and III. In these tests except where indicated a 1:1 molar mixture of TBA and DEG was used. The reactor was charged with 1-2 wt.% catalyst, based on the reactants charged in the autoclave. The reaction was carried out at 200° C. at autogeneous pressure. The time of the reaction and the amount of product, tertiarybutylaminoethoxyethanol (TBEE) are shown in the Tables. Table I shows the results for unsupported catalysts, Tables II and III show the results for supported catalysts.

TABLE I

TBEE SYNTHESIS
(catalytic - batch)

| Unsupported Catalyst | Time, Hrs. | TBEE[1] |
|---|---|---|
| Raney Nickel [Ni—Al] (Aldrich) | 6 | 26.0[2] |
| Nickel [93.4Ni—6.2Al(B-113W)][3] (Degussa) | 5 | 34.3[2] |
| Nickel [92.7Ni—6.9Al(B-113RZ)][3] (Degussa) | 6 | 32.8[2] |
| Nickel [Ni—Al—Mo][3] (Degussa) | 6 | 26.6[2] |
| Nickel [85Ni—9.7Al][3] (Degussa) (BLM-112W) | 6 | 16.0 |
| Raney Copper (Cu—Al)[3] | 20 | 6.4 |
| Raney Cobalt (Co—Al)[3] | 20 | 4.6 |
| Palladium Black | 20 | 1.2 |
| Platinum Black | 20 | 0 |
| RhH [$C_6H_5$)$_3$P]$_4$ | 20 | 0 |
| Copper Chromite (Cu—Cr) | 6 | 1.8 |

[1]Results reported in G.C. area %.
[2]Isolated yields
[3]Raney nickel catalysts are generally prepared by caustic (aqueous NaOH) digestion of Ni/Al alloys [also Cu/Al, Co/Al]. The resulting catalysts are amorphous porous materials, low in aluminum. A description of various leaching techniques and the effect on catalytic activity are given in "Reagents for Organic Synthesis", Fieser and Fieser, Vol. 1, page 723.

TABLE II

TBEE SYNTHESIS
(catalytic - batch)

| Supported Catalyst | BET Surface Area $M^2/g$ | Metal Content wt. basis | Time, Hrs. | TBEE[1] |
|---|---|---|---|---|
| Ni/$Al_2O_3$—$SiO_2$[2] (Harshaw Ni-5132P) | 170 | 65% Ni | 5.5 | 54.0[3] |
| Ni/kieselguhr (Harshaw Ni-0104P) | 125 | 60% Ni | 6 | 32.0 |
| Ni/Propietary support[2] - Harshaw (Ni-3250T) | 150 | 50% Ni | 6 | 22.0 |
| Ni/Proprietary support - Harshaw (Ni-3210T) | 165 | 36% Ni | 6 | 0 |
| Co/Proprietary support - Harshaw (Co-0138E) | 65 | 25% Co | 6 | 0 |
| Co-Proprietary support - Harshaw (Co-0138P) | — | 25% Co | 6 | 0 |
| Co-Proprietary support - Harshaw (Co-0164T) | 60 | 25% Co | 6 | 0 |
| Co/$Al_2O_3$—$SiO_2$ (UCI-G-62) | | 34% Co | 6 | 0 |
| Pt/graphite[2] | | 1% Pt | 6 | 46.4[3] |
| Pt/carbon | | 0.6% Pt | 20 | 30.1 |
| Pt/$Al_2O_3$ | | 1% Pt | 20 | 47.4 |

TABLE II-continued
TBEE SYNTHESIS
(catalytic - batch)

| Supported Catalyst | BET Surface Area M²/g | Metal Content wt. basis | Time, Hrs. | TBEE[1] |
|---|---|---|---|---|
| Pt/SiO₂ | | 0.6% Pt | 40 | 6.9 |
| Pd/carbon | | 5% Pd | 20 | 14.2 |
| Pd/Al₂O₃ | | 0.6% Pd | 20 | 5.0 |

[1] Results are reported in G.C. area %.
[2] TBA/DEG molar ratio = 2.
[3] Isolated yields

TABLE III
TBEE SYNTHESIS
(catalytic - batch)

| Supported Catalyst | Metal Content wt. basis | Time, Hrs. | TBEE[1] |
|---|---|---|---|
| Rh/graphite | 1% Rh | 20 | 38.5 |
| Rh/carbon | 10% Rh | 20 | 24.1 |
| Rh/Al₂O₃ | 1% Rh | 20 | 0 |
| RhCl₃/graphite | 3% Rh | 20 | 25.1 |
| Ru/graphite | 1% Ru | 20 | 20.0 |
| Pd-Pt/Al₂O₃ | 0.1% Pd-0.2% Pt | 20 | 14.6 |
| Rh-Pt/Al₂O₃ | 0.3% Rh-0.3% Pt | 20 | 0.7 |
| Ir-Pt/Al₂O₃ | 0.6% In-0.3% Pt | 20 | 3.0 |
| Al₂O₃ | — | 20 | 0 |

[1] Results reported in G.C. area %.

The tests results in Tables I, II and III show that certain hydrogenation catalysts are effective in catalyzing the amination reaction whereas other known hydrogenation catalysts are either ineffective or provide insignificant yields of the desired product.

EXAMPLE 6

The procedure of Example 1 was carried out with a variety of supported nickel catalysts. The tests were carried out using an equimolar mixture of tertiary butylamine and diethylene glycol. The reaction was carried out at 200° C. and at autogenous pressure. The results are as follows:

| Catalyst | % Ni in Catalyst | % TBEE (G.C. Area) |
|---|---|---|
| Harshaw Ni 3210[1] | 36 | 0 |
| Harshaw Ni 3250[1] | 50 | 22 |
| Harshaw Ni 0104P[2] | 60 | 32 |
| Harshaw Ni 5132P[3] | 65 | 47 |

[1] Ni on proprietary support
[2] Ni on kieselguhr
[3] Ni on Al₂O₃/SiO₂

These data show that the amination reaction is better catalyzed by increasing the nickel content of the catalyst.

EXAMPLE 7

Continuous Amination

The following tests demonstrate the continuous amination process using a fixed bed catalyst reactor. The fixed bed catalyst reactor consists of an elongated tube about 100 mm long and having an internal diameter of about 10 mm. It has a catalyst fill volume of about 8 cc. The reactor has port openings at the lower and upper region to continuously introduce and remove the reaction feed, the reaction product, unreacted reactants, by-products, hydrogen and water. Heating coils are situated around the reactor to heat the catalyst at the desired temperature. The reaction product, unreacted reactants, by-products, hydrogen and water are removed from the upper region of the reactor to a collection vessel where the hydrogen is separated from the liquid by venting and the liquid product, by-products and unreacted reactants are recovered and analyzed. In the tests, the reactor is filled with about 8 cc of catalyst. Glass wool and ceramic beads are placed on top of the catalyst bed to secure the catalyst prior to closing the top of the reactor. Prior to feeding the reactants, hydrogen is introduced into the lower portion of the reactor at ambient temperature and the reactor is gradually heated at the rate of 1° C./min. to the desired activation temperatue (at temperatures above 200° C., the rate is 1° C./3 min) at which point the temperature is maintained during activation. Following activation the reactor is gradually cooled at the rate of 1° C./min to 140° C. whereupon the reactants are fed into the reactor at a flow rate ranging from 10 to 160 ml/hr. When liquid reaches the outlet port, the reactor is again gradually heated to the target temperature at the rate of 1° C./min and held at this temperature during the course of the test. The designated space velocity is ascertained from the flow rate divided by the catalyst bed reactor volume (i.e., 8 cc). From this data the superficial residence time is obtained. The reaction products, unreacted reactants and by-products are analyzed by calibrated gas chromatography. The product was isolated by vacuum distillation.

In the following tests, various hydrogenation catalysts were evaluated using the reactor and reaction conditions described in the preceeding paragraphs. The reactants used were tertiarybutylamine (TBA) and diethylene glycol (DEG) which were metered in the reactor at a 1:1 molar ratio. Hydrogen gas was flowed through the catalyst bed reactor cocurrently with the reactants at a flow rate of 1500 SCF/B (standard cubic feet/barrel) i.e., hydrogen flow rate of 4.3 liter/hr. (STP) for a space velocity of 2 or 8.6 l/hr. (STP) for a space velocity of 4. The amount of the reaction product, tertiarybutylaminoethoxyethanol (TBEE) and the undesired by-product, N-tertiarybutyl-morpholine (TBM) are set forth in Table IV for each of the catalyst runs. The results of these tests are also set forth in Table IV.

TABLE IV
TBEE SYNTHESIS
(catalytic - fixed bed)

| Catalyst | Bed Temp., °C. | H₂ Flow Rate (SCF/B Reactants) | Space Velocity (V/V/hr.) | Product (G.C. Area, %) | | |
|---|---|---|---|---|---|---|
| | | | | TBEE | DEG | TBM |
| Ni/Al₂O₃—SiO₂[1] | 210 | 1500 | 4 | 61 | 18 | 21 |
| Ni/Al₂O₃—SiO₂[1] | 193 | 1500 | 2 | 43 | 29 | 26 |
| Ni—Cu—Co—SiO₂/ | | | | | | |

TABLE IV-continued

TBEE SYNTHESIS
(catalytic - fixed bed)

| Catalyst | Bed Temp., °C. | $H_2$ Flow Rate (SCF/B Reactants) | Space Velocity (V/V/hr.) | Product (G.C. Area, %) | | |
|---|---|---|---|---|---|---|
| | | | | TBEE | DEG | TBM |
| kieselguhr[2] | 250 | 1500 | 2 | 32 | 51 | 13 |
| Pt/Al$_2$O$_3$[3] | 250 | 1500 | 2 | 29 | 65 | 6 |
| Cu—Cr/SiO$_2$[4] | 218 | 1500 | 4 | 2 | 96 | <2 |

[1]Ni/Al$_2$O$_3$—SiO$_2$ is 65% Ni on a Al$_2$O$_3$—SiO$_2$ (Harshaw - 5132P).
[2]Ni—Cu—Co—SiO$_2$/kieselguhr is a coprecipitated catalyst prepared in accordance with U.S. Pat. No. 4,263,225 and available from UCI as Catalyst 2330.
[3]Pt/Al$_2$O$_3$ is 0.6% Pt on Al$_2$O$_3$ support.
[4]Cu—Cr/SiO$_2$ is 25% CuO, 1% Cr$_2$O$_3$, 0.1% Na$_2$O, 70% SiO$_2$, about 4% H$_2$O (BASF-H3-10).

EXAMPLE 8

The reactor and experimental procedure described in Example 7 were repeated except that the activation procedure was varied. The reactor contained 8 cc of the designated catalyst. The reactants, tertiarybutylamine (TBA) and diethylene glycol (DEG) were fed into the reactor at a mole ratio of TBA/DEG of 2:1. Hydrogen was fed continuously into the reactor at 5 1/hr (STP). The reaction was carried out at 5 MPA pressure. The results of these tests are shown in Table V along with the activation conditions, reactions temperatures, and space velocities.

TABLE V

| | $H_2$ Activation | | Reaction Temp., °C. | Space Velocity V/V/hr | Experimental Results | | |
|---|---|---|---|---|---|---|---|
| | °C. | Hr. | | | Yield[1] % TBEE | Selectivity EETB/TBM | DEG Consumed Mole/hr/1 liter |
| Ni—Cu—Co/SiO$_2$/Kieselguhr[2] | | | | | | | |
| 20 × 40 mesh | 350 | 2 | 200 | 4.0 | 40 | 4.3 | 6.5 |
| 20 × 40 mesh | 200 | 4 | 200 | 4.8 | 10 | 34 | 1.6 |
| 1/12" pellets | 200 | 2 | 200 | 2.0 | 5 | 13 | 1.1 |
| Ni/Al$_2$O$_3$—SiO$_2$[3] | 186 | 16 | 200 | 4.8 | 25 | 5.9 | 4.6 |
| Ni—Cu—Co/SiO$_2$—Al$_2$O$_3$/Kieselguhr[4] | 200 | 16 | 200 | 4.8 | 0.9 | 303 | 0.14 |
| id[5] | 200 | 16 | 246 | 2.0 | 30 | 1.7 | 2.4 |
| Cu—Cr/SiO$_2$[6] | 250 | 1 | 200 | 4.8 | 0 | 0 | <0.005 |
| Co/Al$_2$O$_3$—SiO$_2$[7] | 350 | 2 | 200 | 4.0 | 23 | 3.0 | 4.0 |

[1]Mole Fraction of DEG Converted to TBEE
[2]Ni—Cu—Co/SiO$_2$/Kieselguhr is a coprecipitated catalyst prepared in accordance with U.S. Pat. No. 4,263,225 and available from UCI as Catalyst 2230.
[3]Ni/Al$_2$O$_3$—SiO$_2$ is 65% Ni on Al$_2$O$_3$—SiO$_2$ (Harshaw 5132-P) which has been prereduced and stabilized.
[4]Ni—Cu—Co/SiO$_2$—Al$_2$O$_2$/Kieselguhr is a coprecipitated catalyst prepared in accordance with U.S. Serial No. 388,966; filed June 16, 1982
[5]Reaction carried out at 246° C.
[6]Cu—Cr/SiO$_2$ is 25% CuO, 1% Cr$_2$O$_3$, 0.1% Na$_2$O, 70% SiO$_2$, about 4% H$_2$O (BASF-H3-10).
[7]Co/Al$_2$O$_3$—SiO$_2$ contains about 34% Co (UCI-G-62).

EXAMPLE 9

The procedure described in Example 7 was repeated using the Ni—Cu—Co/SiO$_2$/kieselguhr (Trimetallic 2330) catalyst reduced and activated with hydrogen at 200° C. Tertiarybutylamine (TBA) and diethylene glycol (DEG) were used as the reactants at a 2:1 molar ratio. The amination reaction was carried out at various space velocities and the reaction product, tertiarybutylaminoethoxyethanol (TBEE) and the undesired by-product, N-tertiarybutyl morpholine (TBM) were analyzed. The results of the tests with two different catalyst sizes shown in FIG. 1 indicate diffusion limits for TBEE production. These tests show that the residence time is critical in maximizing the selective production of TBEE concurrent with the minimal production of the by-product TBM. Thus, a superficial space velocity ranging from 1.5 v/v/hr to 3.5 appears to be optimal in achieving the desired amination. This translates to a superficial residence time ranging from 0.29 to about 0.67 hr., preferably from about 0.35 hr. to about 0.55 hr.

EXAMPLE 10

The procedure of Example 9 was repeated except that the reaction was carried out at different temperatures with a space velocity of 4/hr. and varying the space velocity at a reaction temperature of 220° C. The results of these tests are shown in FIG. 2 where the degree of conversion of diethylene glycol is plotted against the selectivity of producing TBEE. These data show the relationship of temperature and space velocity (residence time) on the selective production of TBEE.

EXAMPLE 11

Several tests were carried out to determine the effect of hydrogen in the amination reaction. In the absence of hydrogen, the trimetallic catalyst (T-2330, Ni—Co—Cu/SiO$_2$/kieselguhr) is deactivated about 50% for a reaction time of about 60 hrs. at 200° C. with a linear hour space velocity of 4 in a fixed-bed reactor; but it was deactivated about 12% in the presence of hydrogen under the same reaction conditions. In addition to faster catalyst deactivation, the absence of hydrogen resulted in a dark brown product stream whereas the presence of hydrogen gave a clear product. In the presence of hydrogen, hydrogen flow rates ranging from 1 liter (STP)/hr (175 SCF/B) to 5 liters (STP)/hr (875 SCF/B) did not affect the catalyst deactivation, product quality and TBEE yield.

What is claimed is:

1. A process for selectively producing a severely sterically hindered secondary aminoether alcohol comprising reacting:

(a) a primary amino compound having the general formula

where $R_1$ is selected from the group consisting of secondary or tertiary alkyl radicals having 3 to 8 carbon atoms and cycloalkyl radicals having 3 to 8 carbon atoms, with (b) a polyalkenyl ether glycol having the general formula:

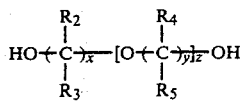

where $R_2$, $R_3$, $R_4$ and $R_5$ are each independently selected from the group consisting of hydrogen, $C_1$ to $C_4$ alkyl radicals, and $C_3$–$C_8$ cycloalkyl radicals, with the proviso that if the carbon atom of $R_1$ directly attached to the nitrogen atom is secondary, at least one of $R_2$ and $R_3$ directly bonded to the carbon which is bonded to the hydroxyl group is an alkyl or cycloalkyl radical, x and y are each positive integers independently ranging from 2 to 4, and z is a positive integer ranging from 1 to 4, said process being carried out in the presence of a catalytically effective amount of a Group VIII metal containing supported hydrogenation catalyst at elevated temperatures and pressures, and wherein the mole ratio of amino compound to polyalkenyl ether glycol is less than 2:1 when z is greater than 1.

2. The process of claim 1 wherein $R_1$ is an alkyl radical having 4 to 6 carbon atoms, $R_4$ and $R_5$ are hydrogen, and x is 2.

3. The process of claim 2 wherein $R_1$ is tertiary butyl, $R_2$ and $R_3$ are hydrogen and y is 2.

4. The process of claim 3 wherein z is 1.

5. The process of claim 1 wherein the reaction is carried out at a temperature ranging from about 160° to about 425° C. and at a pressure ranging from about 50 to about 3000 psig.

6. The process of claim 5 wherein the reaction is carried out at a temperature ranging from about 180° to about 400° C. and at a pressure ranging from about 100 to about 1000 psig.

7. The process of claim 6 wherein the reaction is carried out at a temperature ranging from about 190° to about 350° C. and at a pressure ranging from about 150 psig to about 750 psig.

8. The process of claim 4 wherein the reaction is carried out at a temperature ranging from about 190° C. to about 350° C. and at a pressure ranging from about 150 psig to about 750 psig.

9. The process of claim 1 wherein the hydrogenation catalyst is a nickel, a cobalt, a nickel-cobalt-copper, or a platinum catalyst all of which are supported on alumina, silica or alumina-silica.

10. The process of claim 8 wherein the hydrogenation catalyst is a nickel, a cobalt, a nickel-cobalt-copper, or a platinum catalyst all of which are supported on alumina, silica, or alumina-silica.

* * * * *